(12) United States Patent
Leventhal

(10) Patent No.: US 11,445,840 B1
(45) Date of Patent: Sep. 20, 2022

(54) DRINK CADDY

(71) Applicant: Adam Michael Leventhal, Aliso Viejo, CA (US)

(72) Inventor: Adam Michael Leventhal, Aliso Viejo, CA (US)

( * ) Notice: Subject to any disclaimer, the term of this patent is extended or adjusted under 35 U.S.C. 154(b) by 196 days.

(21) Appl. No.: 17/016,012

(22) Filed: Sep. 9, 2020

Related U.S. Application Data

(60) Provisional application No. 62/901,079, filed on Sep. 16, 2019.

(51) Int. Cl.
*A47G 23/02* (2006.01)
*B65D 25/22* (2006.01)

(52) U.S. Cl.
CPC ............ *A47G 23/02* (2013.01); *B65D 25/22* (2013.01)

(58) Field of Classification Search
CPC .... A47G 23/02; A45F 2200/0583; A61J 1/16; B65D 25/22
USPC .......................... 206/170, 174; 220/737, 738
See application file for complete search history.

(56) References Cited

U.S. PATENT DOCUMENTS

| | | | | |
|---|---|---|---|---|
| 2,396,473 A | * | 3/1946 | Powell | B65D 71/0059 206/170 |
| 3,893,607 A | * | 7/1975 | Jones | B65D 71/0011 224/653 |
| 4,428,484 A | * | 1/1984 | Rattay | A45C 13/02 206/548 |
| 5,508,494 A | * | 4/1996 | Sarris | A47J 31/005 219/385 |
| 5,860,525 A | * | 1/1999 | Bellehchili | B65D 31/12 206/443 |
| 7,357,247 B2 | * | 4/2008 | Guenther | B65D 71/50 206/139 |
| 7,624,886 B2 | * | 12/2009 | Huang | A45C 7/0036 220/6 |
| D714,059 S | | 9/2014 | Blackwell et al. | |
| 2006/0011686 A1 | * | 1/2006 | Latham | B60R 7/04 190/102 |
| 2006/0102498 A1 | * | 5/2006 | Guenther | B65D 71/50 206/139 |
| 2007/0017828 A1 | * | 1/2007 | Cuomo | B65D 71/0014 206/170 |
| 2007/0175787 A1 | * | 8/2007 | Lown | A45F 3/16 206/427 |
| 2008/0083629 A1 | * | 4/2008 | Soucie | A45C 3/04 206/139 |
| 2009/0256038 A1 | * | 10/2009 | Schaefer | A47G 23/0225 220/737 |

* cited by examiner

*Primary Examiner* — Jacob K Ackun
(74) *Attorney, Agent, or Firm* — Plager Schack LLP; Mark H. Plager; Naomi Mann

(57) ABSTRACT

A drink caddy comprising a compartment section configured for holding a drink and a size adjustable cord which can be wrapped around the drink, in order to secure the drink within the compartment section and avoid spilling during transport. According to various embodiments, the drink caddy may comprise multiple compartment sections for transporting multiple drinks of varying sizes.

10 Claims, 4 Drawing Sheets

DRINK CADDY

RELATED APPLICATION

This application claims priority to provisional patent application U.S. Ser. No. 62/901,079 filed on Sep. 16, 2019, the entire contents of which is herein incorporated by reference.

BACKGROUND

The embodiments herein relate generally to devices and methods for carrying and transporting drinks, and more specifically to such devices and methods which prevent drinks from spilling during transport.

Carriers for beverage filled containers (i.e. drinks) may include multiple compartments to facilitate simultaneous transport of a number of drinks. Typically, each drink may be individually placed in a compartment of the carrier. However, agitation during transport may cause drinks to spill and/or fall out of the carrier device, particularly if the drink does not fit within the compartment. As such, an improved system for transporting multiple drinks is needed.

SUMMARY

According to various embodiments, disclosed is a carrier for drinks, or drink caddy, which includes at least one strap to secure and/or stabilize a drink held within the container. Thus, a user may transport drinks within the container with a lower risk of spilling the drinks or having the drinks fall out of the drink caddy.

In embodiments, the drink caddy may include multiple compartments, for holding multiple drinks within the drink caddy, and may further include a strap to secure/ stabilize the drink within the compartment. Each of the compartments may be configure to hold one drink. The strap(s) may be size adjustable and configured to fasten around the drink in order to avoid spilling. In some embodiments, the strap may comprise a Bungee cord which may be size adjustable via a locking clasp.

In further embodiments, the caddy may comprise a handle for facilitating transport of the drinks. Additionally, the caddy may comprise a pocket, which may be used for holding packets of sugar, powdered milk, change, etc. The pocket may be closable via a zipper or other closure element. In further embodiments, the caddy may include at least one straw holder. According to an exemplary embodiment, the drink caddy may include 4 compartments for carrying up to 4 drinks. In yet further embodiments, the drink caddy may be made out of a polyester material, and may be reusable and collapsible.

Thus, the drink carrier may be used to securely carry a multiple number of drinks, and avoid spilling. Moreover, as each strap may be adjusted to the size of the drink, the present disclosure enables different sized drinks to be carried, with reduced risk of spilling or dropping the drinks.

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

In the following detailed description of the invention, numerous details, examples, and embodiments of the invention are described. However, it will be clear and apparent to one skilled in the art that the invention is not limited to the embodiments set forth and that the invention can be adapted for any of several applications.

With reference to the accompanying figures, and in accordance with various embodiments, disclosed is a drink carrier or caddy, which includes at least one strap or cord for securing drinks held within the container. The cord enables drinks, which may be of varying sizes and design, to be held within the caddy and transported with reduced risk of spillage.

Figure 1:
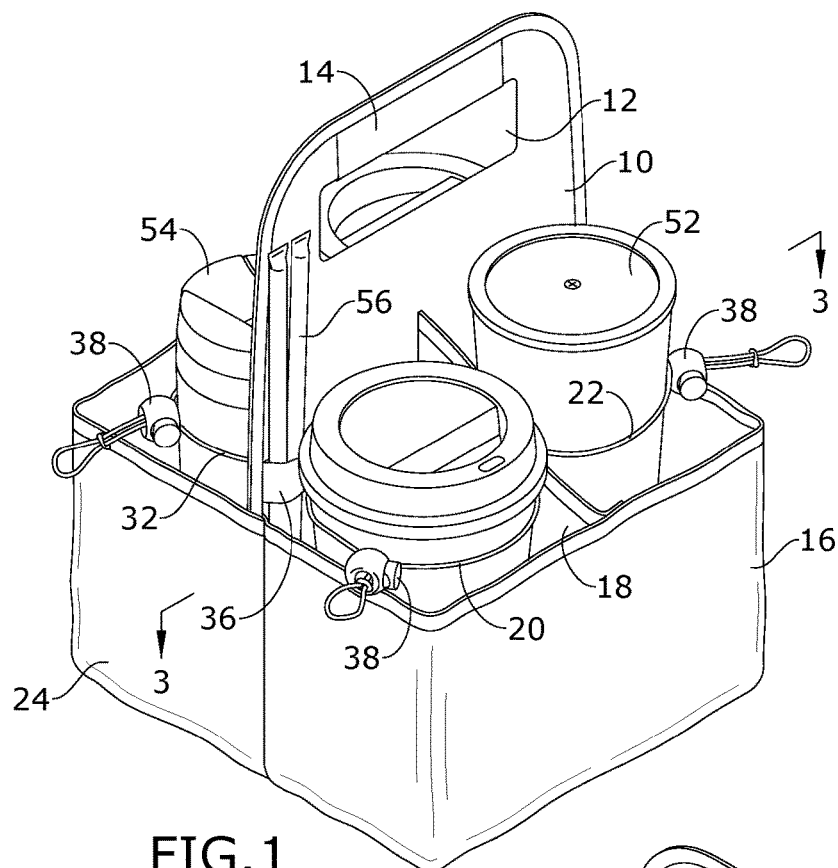
FIG. 1 is a front perspective view of a drink caddy, in accordance with an exemplary embodiment, wherein multiple drinks are shown held within compartments of the caddy.
Figure 2:
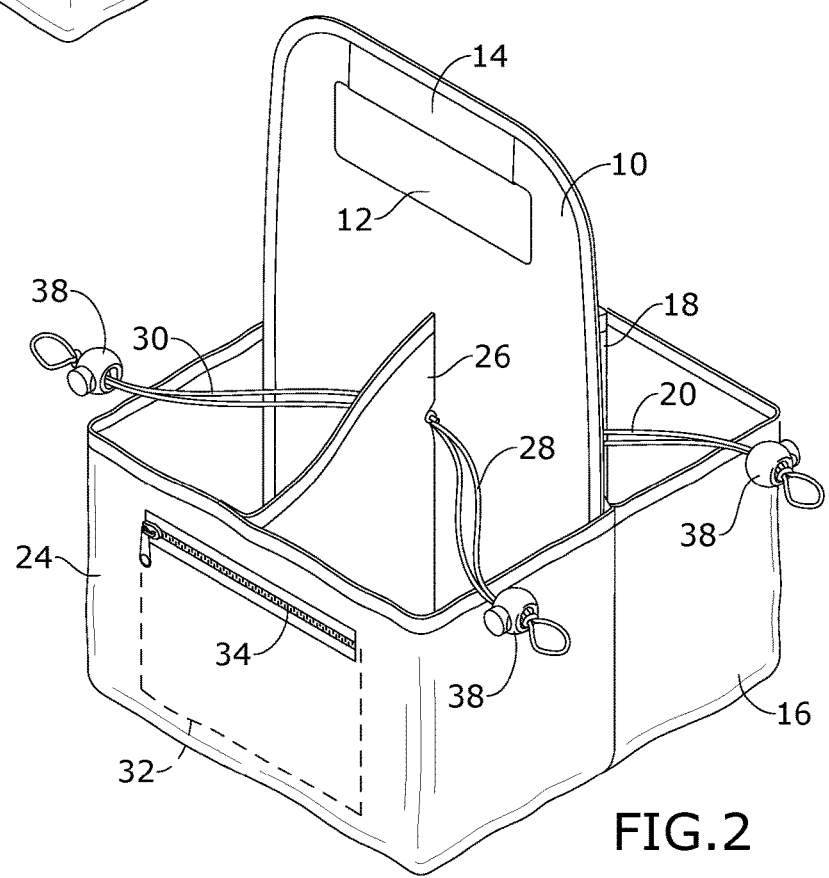
FIG. 2 is a rear perspective view of the drink caddy of FIG. 1, shown without the drinks.
Figure 3:
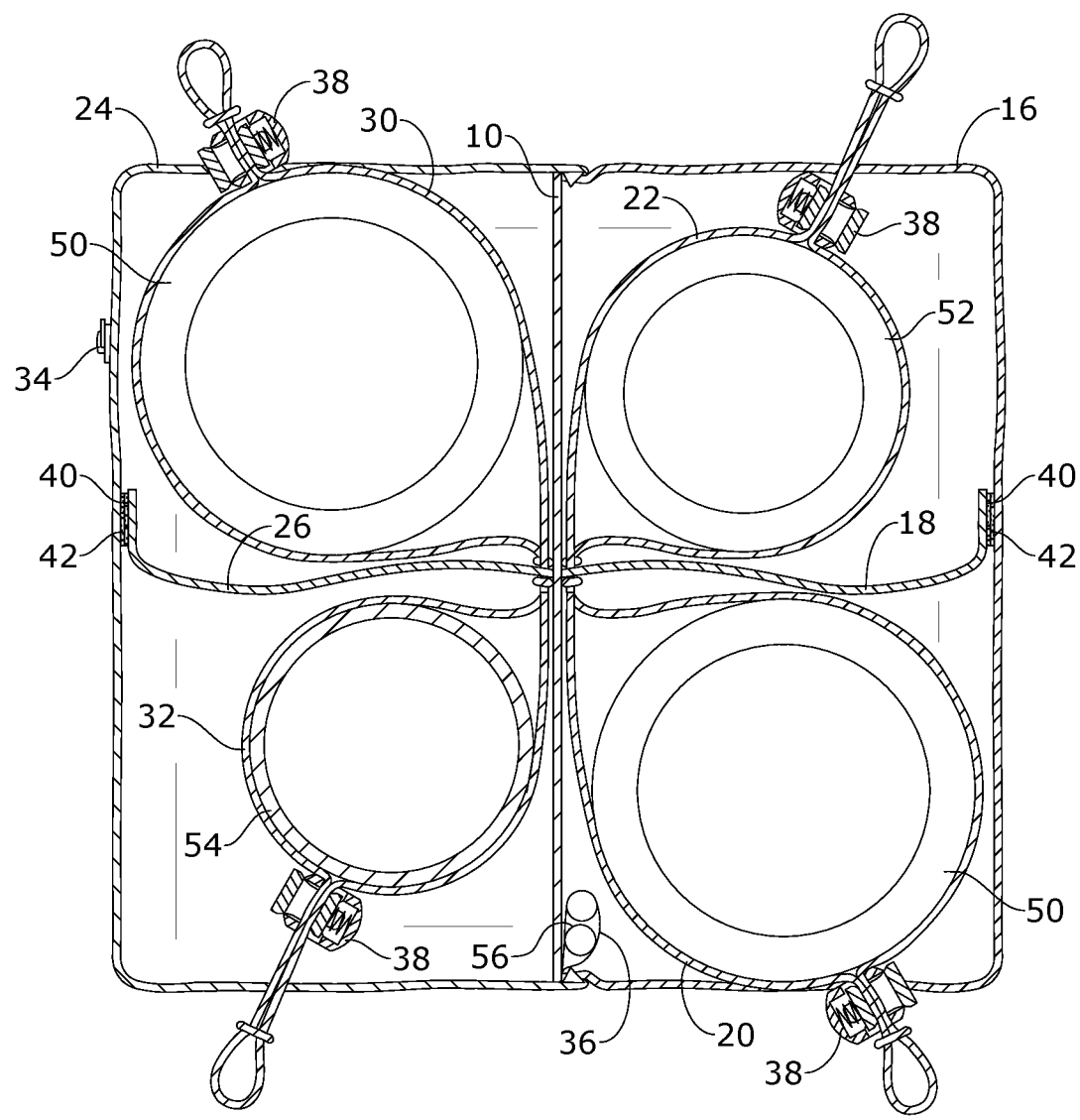
FIG. 3 is a section view of the drink caddy, taken along line 3-3 in FIG. 1, illustrating each of the cords adjusted to fit varying cup sizes.

The caddy may generally comprise multiple compartments, wherein each compartment may be sized to hold a single drink. According to an exemplary embodiment, the caddy may comprise 4 compartments. As shown in FIGS. 1-3, the caddy may include a front compartment 16, and a rear compartment 24, which may be divided by a center panel 10. A front compartment divider 18 may form two front compartment sections for holding two drinks (e.g. a drink cup 52, and a coffee cup 50) within the front compartment 16 of the caddy. A rear compartment divider 26, may form two rear compartment sections for holding two more drinks (e.g. a tumbler 54, and another coffee cup 50) within the rear compartment 24 of the caddy.

In embodiments, the front compartment divider 18 may extend perpendicularly from the center panel 10 to an approximate central line 42 of the front compartment 16. An end 40 of the divider 18 may be attached along the central line 42 of the front compartment 16. The rear compartment divider 26 may similarly extend perpendicularly from the center panel 10 to an approximate central line 42 of the rear compartment 24. An end 40 of the divider 26 may be attached along central line 42 of the rear compartment 24. Thus, the center panel 10, front compartment divider 18 and rear compartment divider 26 may be arranged to form 4 drink compartment sections within the caddy.

In embodiments, the caddy may comprise straps or looped cords that extend in to the compartment sections for holding the drinks in a stabilized position within the caddy. According to an exemplary embodiment, and as best shown in FIG. 3, the caddy may comprise a first cord 20 and a second cord 22 for holding the drinks (e.g. drink cup 52, and coffee cup 50), within the sections of front compartment 16. The caddy may further comprise a third cord 28 and a fourth cord 30 for holding drinks (e.g. tumbler 54, and coffee cup 50), within the sections of rear compartment 24.

Each cord may be attached to the center panel 10, and/or dividers forming the walls of the compartment section. In some embodiments, each cord may be attached at an intersection of the center pane 10 and divider 18 or 26, forming the compartment section. In further embodiments, each cord may be placed a few inches above the bottom of the caddy. According to various embodiments, each cord may be placed at a height of at least 2 inches, or at least 3 inches, or at least 4 inches, or at least 5 inches. In embodiments, the cords may be attached at a height approximately equal to the height extension of the compartment walls. The caddy may comprise a cord for each compartment of the caddy. For example, a caddy comprising 4 compartments may include 4 cords, as shown in the figure.

Figure 4:
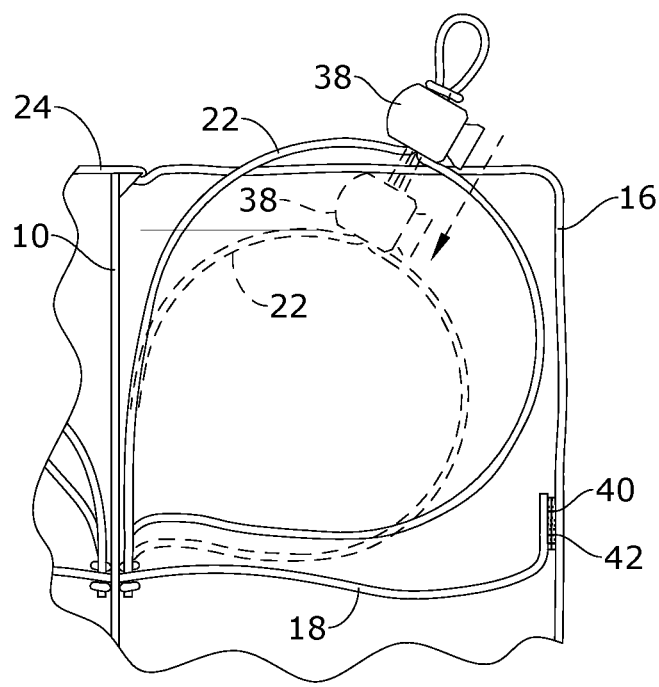
FIG. 4 is a detail top view of the drink caddy, illustrating an adjustment of a loop size of one of the cords via a cord lock.

With particular reference to FIG. 4, the cords 20, 22, 28, 40, may each be size adjustable. For example, each cord may include a cord lock 38, (also known as a cord fastener, spring clasp, or cord toggle) which allows the cord to be adjusted to the size of the beverage, and locked into place. Such cord lock may include a spring biased release button which, when engaged, allows the cord to be moved thought the cord lock in order to adjust its length or circumference. Once disengaged, the circumference of the cord is fixed via the cord lock.

Figure 5:
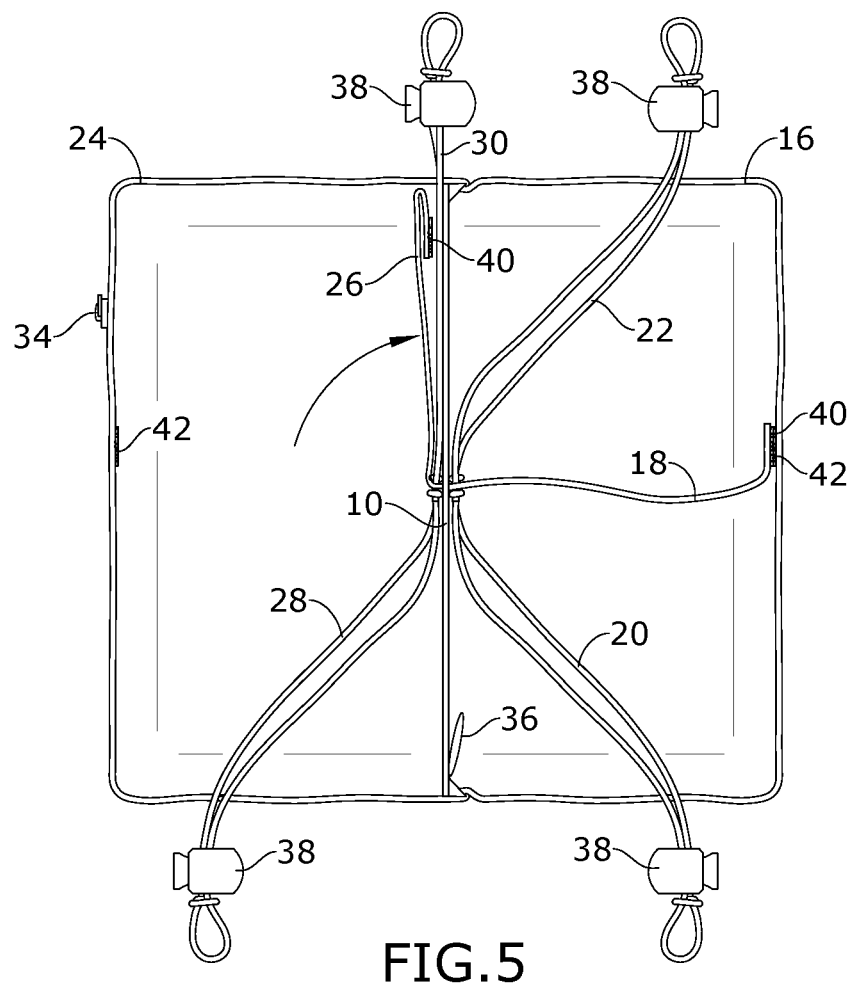
FIG. 5 is a top view of the drink caddy, illustrating a folding of one of the dividers of the caddy.
Figure 6:
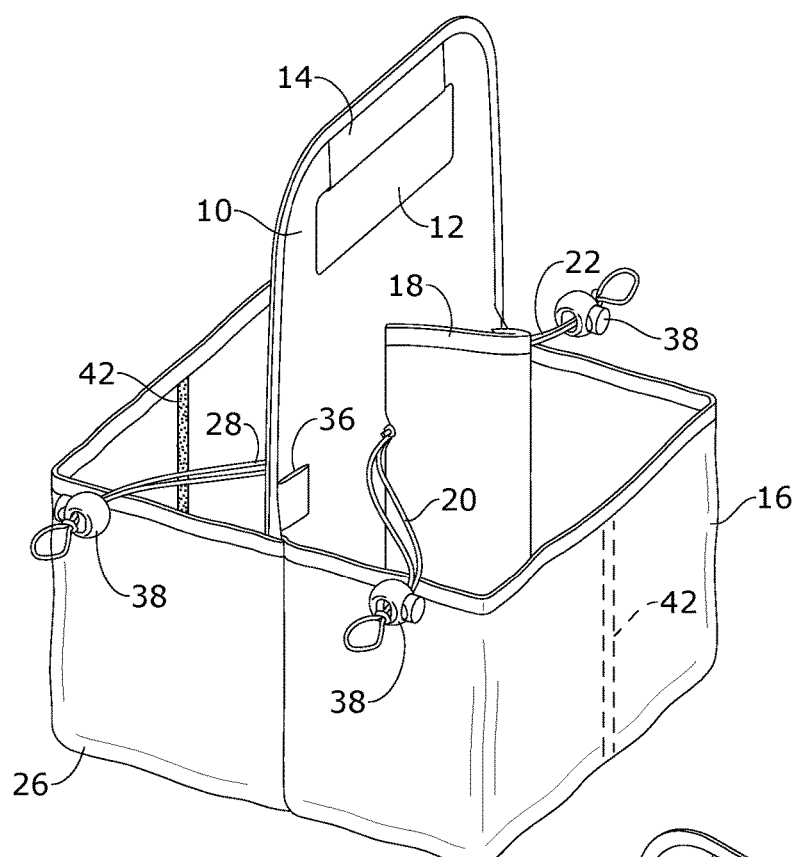
FIG. 6 is a front perspective view of the caddy with the dividers shown in a folded position.

In some embodiments, the end 40 of the front compartment divider 18 may further be detachable from the central line 42 of the front compartment 16. Additionally, the end 40 of the rear compartment divider 26 may be detachable from the central line 42 of the rear compartment 24. In further embodiments, ends 40 of dividers 18 and 26 may further be attachable to the central divider 10 (see FIGS. 5 and 6). For example, central lines 42, ends 40, and/or center panel 10 may comprise hook and loop fastener strips or Velcro® attachment elements. As such, either one or both of the dividers 18 and 26 may be folded, as shown in the figures. This may enable a user to carry other items, which may not fit in a compartment section. For example, as shown in FIG. 5, divider 26 has been folded while divider 18 remains attached to create space for 2 drinks in the front compartment 16, while leaving a larger space in the rear compartment 24 (e.g. for carrying a lunch item such as a sandwich). Additionally, the front and rear compartments 16, 24, may be made out of a foldable material, i.e. polyester. Thus, folding of the dividers 18, 26, may enable the caddy to be folded or collapsed.

In some embodiments, the caddy may comprise a handle 14 for facilitating transport. According to an exemplary embodiment, a handle opening 12 may be formed around a top section of the center panel 10, to form handle 14 in the top portion of panel 10, as shown in the figures.

Figure 7:
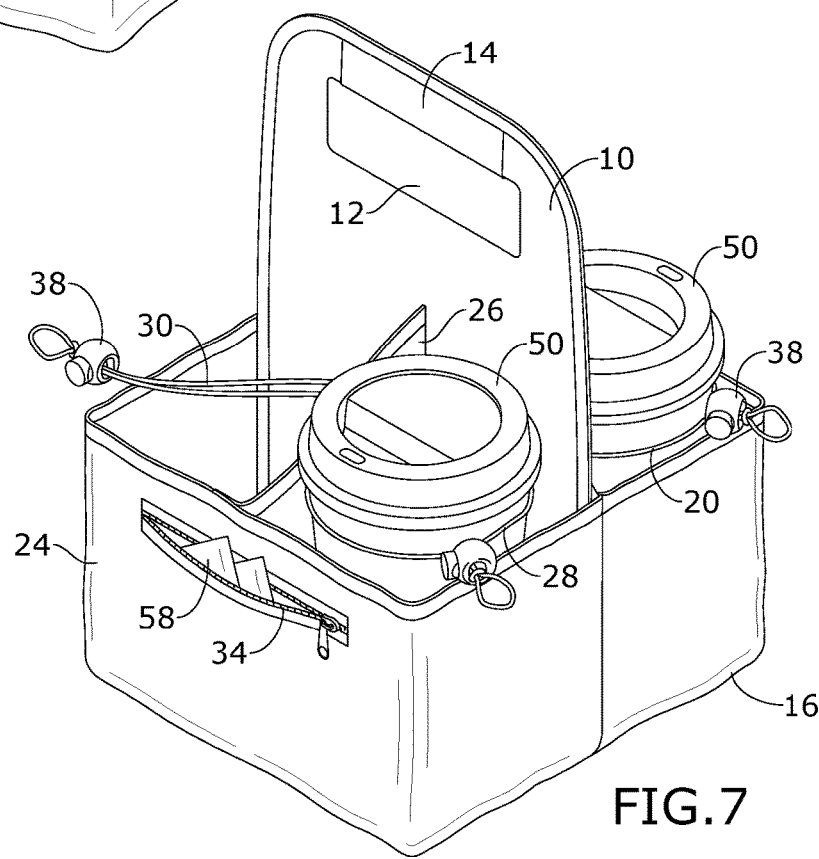
FIG. 7 is a rear perspective view of the caddy, shown in use and with the pocket zipper open.

In further embodiments, the caddy may comprise a pocket 32 for carrying small items such as packets 58 (e.g. sugar or cream packets), change, and the like. As shown in the figures, the pocket 32 may be closable. For example, pocket 32 may comprise a closure element such as a zipper 34 as shown in FIGS. 2 and 7. In further embodiments, the caddy may comprise one or more straw holders 36, which may comprise loops configured for holding straws 56. According to an exemplary embodiment, the carrier may be made out of a flexible material, such as polyester, e.g. 600D polyester. Thus, the caddy may be reusable and/or collapsible/ foldable.

A user may place various drinks within each compartment section of the caddy, and wrap a cord around each drink. The user may then adjust the size of the cord to tighten the cord around the drink via the cord lock. Thus, drinks placed within the caddy may be securely carried, regardless of the size of the drink with respect to the size of the compartment section.

The constituent elements of the disclosed device and system listed herein are intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device. Terms such as 'approximate,' 'approximately,' 'about,' etc., as used herein indicate a deviation of within +/−10%. Relationships between the various elements of the disclosed device as described herein are presented as illustrative examples only, and not intended to limit the scope or nature of the relationships between the various elements. Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A drink caddy comprising:
   a first compartment section and a first cord extending into the first compartment section,
   wherein the first compartment section is configured to hold a drink,
   and wherein the first cord is size adjustable and configured to wrap around said drink to secure said drink within the first compartment section, and to reduce the risk of spilling during transport of the drink within said drink caddy.

2. The drink caddy of claim 1, further comprising:
   a second compartment section and a second cord extending into the second compartment section;
   a third compartment section and a third cord extending into the third compartment section; and
   a fourth compartment section and a fourth cord extending into the fourth compartment section,
   wherein the second compartment section, the third compartment section, and the fourth compartment section are each configured to hold a drink,
   wherein the second cord, the third cord, and the four cord are each size adjustable and configured to wrap around a drink, and
   wherein the caddy is configured to securely transport multiple drinks.

3. The drink caddy of claim 2, further comprising:
   a front compartment;
   a rear compartment,
   a center panel between the front compartment and rear compartment;
   a front compartment divider, coupled between said center panel and a wall of said front compartment,
   a rear compartment divider, coupled between said center panel and a wall of said rear compartment,
   wherein said front compartment divider is perpendicular to the center panel and extends from the center panel to said wall of the front compartment to form said first compartment section and said second compartment section,
   wherein said rear compartment divider is perpendicular to the center panel and extends from the center panel to said wall of the rear compartment to form said third compartment section and said fourth compartment section.

4. The drink caddy of claim 3, wherein the front compartment divider is attachable to and detachable from said wall of the front compartment.

5. The drink caddy of claim 4, wherein the caddy is reusable and foldable.

6. The drink caddy of claim 3, further comprising a handle formed within said center panel.

7. The drink caddy of claim 3, further comprising a straw holder formed within said center panel.

8. The drink caddy of claim 3, wherein said front compartment and said rear compartment are made of a flexible material.

9. The drink caddy of claim 3, further comprising a pocket formed within an outer wall of at least one of said front compartment or rear compartment.

10. The drink caddy of claim 1, wherein the first cord comprises a bungee cord with a cord lock.

* * * * *